United States Patent
Hayashizaki et al.

[11] Patent Number: 6,120,667
[45] Date of Patent: Sep. 19, 2000

[54] MULTI-CAPILLARY ELECTROPHORESIS APPARATUS

[75] Inventors: Yoshihide Hayashizaki, Ibaraki; Shin Nakamura; Katsuya Kashiwagi, both of Kyoto, all of Japan

[73] Assignees: Japan Science and Technology Corporation, Kawaguchi; The Institute of Physical and Chemical Research, Wako; Shimadzu Corporation, Kyoto, all of Japan

[21] Appl. No.: 09/006,933

[22] Filed: Jan. 14, 1998

[30] Foreign Application Priority Data

Jan. 16, 1997  [JP]  Japan .................................. 9-019968
Jan. 16, 1997  [JP]  Japan .................................. 9-019969

[51] Int. Cl.⁷ .................................................. G01N 27/26
[52] U.S. Cl. ........................................ 204/603; 356/344
[58] Field of Search ............................ 204/452, 603, 204/461, 612; 356/344; 382/128, 129

[56] References Cited

U.S. PATENT DOCUMENTS

| | | | |
|---|---|---|---|
| 4,592,089 | 5/1986 | Hartman ........................ | 382/6 |
| 5,221,448 | 6/1993 | Weinberger et al. ............... | 204/180.1 |
| 5,534,703 | 7/1996 | Kambara et al. .................... | 250/458.1 |
| 5,538,613 | 7/1996 | Brumley et al. ..................... | 204/612 |
| 5,582,705 | 12/1996 | Yeung et al. ....................... | 204/603 |
| 5,885,430 | 3/1999 | Kernan et al. ....................... | 204/453 |

FOREIGN PATENT DOCUMENTS 9317325   9/1993   WIPO .

OTHER PUBLICATIONS

WPIDS abstract of Hitachi LTD (JP 05196602 A), Aug. 1993.

*Primary Examiner*—Jill Warden
*Assistant Examiner*—Alex Noguerola
*Attorney, Agent, or Firm*—Armstrong, Westerman, Hattori, McLeland & Naughton

[57] ABSTRACT

After a sample stage moves and brings a sample titer plate toward and into contact with a capillary array end, a high voltage is applied across electrodes for a prescribed time for injecting samples. Thereafter an electrophoresis reservoir comes into contact with the capillary array end, for starting electrophoresis. When electrophoresed/separated DNA fragments pass through a detection part, an excitation/photoreceiving optical system is scanned so that photomultipliers detect fluorescence from four types of fluorescent materials labeling the samples. The excitation/photoreceiving optical system comprises an epi-optical system and a confocal optical system, and is scanned at a high speed.

11 Claims, 10 Drawing Sheets

MULTI-CAPILLARY ELECTROPHORESIS APPARATUS

BACKGROUND OF THE INVENTION

1. Field of the Invention

The present invention relates to an online electrophoresis apparatus for determining base sequences by electrophoresing DNA fragment samples and detecting fluorescence from the samples during the electrophoresis. Primers or terminators of the DNA fragment samples are labeled by the Sanger's method. More specifically, the present invention relates to an electrophoresis apparatus called a multi-capillary DNA sequencer for simultaneously electrophoresing a plurality of samples by employing a plurality of capillary columns charged with electrophoresis gels.

2. Description of the Background Art

A DNA sequencer having high sensitivity, a high speed and high throughput is necessary for determining the base sequences of DNAs such as human genomes, which have long base sequences. Accordingly, a multi-capillary DNA sequencer that has a plurality of capillary columns charged with gels is proposed in place of those employing flat plate type slab gels. As compared with the slab gels, the capillary columns can readily handle, inject and electrophorese samples at a high speed and make highly sensitive detections. If a high voltage is applied in slab gels, bands are spread due to the influence of Joulean heat, or temperature gradients are caused. Conversely, capillary columns have no such problems but make highly sensitive detections with minimal spreading of bands under high-speed electrophoresis with the application of a high voltage.

A treatment by the Sanger's method results in the formation of four types of DNA fragment samples having ends consisting of A (adenine), G (guanine), T (thymine) and C (cytosine). In order to increase the throughput, it is necessary to electrophorese the samples in a plurality of capillary columns. When a set of samples of end bases are electrophoresed in different capillary columns, however, differences between the electrophoresis speeds of the capillary columns result in errors of base sequence determination. Therefore, a set of samples containing DNA fragments of four types of end bases must be injected into each capillary column. In this case, each capillary column labels the four types of DNA fragments of different end bases with at least two types of fluorescent materials in order to distinguish the fragments from each other.

A method has been proposed (refer to Anal. Chem. 1994, 66, pp. 1021–1026 (reference 1)) employing four types of fluorophores FAM, JOE, TAMRA and ROX as labels for different DNA fragments in order to distinguish the DNA fragments of different end bases. A method has also been proposed (refer to Anal. Chem. 1992, 64, pp. 2149–2154 (reference 2)) employing two types of fluorophores FAM and JOE in different ratios for distinguishing four types of DNA fragments from each other through coding. Both cases provide examples of samples containing four types of DNA fragments of different end bases being injected into each capillary column in order to increase the throughput of a multi-capillary DNA sequencer. DNA fragments of different end bases can be distinguished from each other by multi-color fluorescent labels and a plurality of samples can be simultaneously electrophoresed in a plurality of capillary columns.

Samples are simultaneously electrophoresed in a plurality of capillary columns, so that an optical system detects fluorescence generated from the samples. An example of such an optical system introduces an excitation light beam from the side of an array of the capillary columns and detects the generated fluorescence with a CCD (charge-coupled device) camera which is positioned perpendicularly along the capillary column array (refer to reference 1). In order to eliminate background signals based on scattering on the surfaces of the capillary columns, the electrophoresed samples are rendered to form sheath flows on positions irradiated with the excitation beam in the exterior of the capillary columns.

While the beam intensity is less damped in the method of reference 1 due to the formation of the sheath flows, it is difficult to position the capillary columns for implementing the sheath flow states, and multiplication is hard to attain.

Another exemplary optical system condenses excitation light in order to irradiate a single capillary column in an excitation optical system, for detecting fluorescence from samples in the capillary column by a photoreceiving optical system. Both excitation and photoreceiving optical systems are fixed in such a way as to perpendicularly scan an array of a plurality of capillary columns, thereby successively detecting fluorescence from samples in the capillary columns (refer to reference 2).

In the method of reference 2, however, the capillary array is mechanically moved in order to be scanned, resulting in the capillary columns being twisted so that the number thereof tends to be restricted.

In each of these methods, the number of capillary columns for simultaneously performing electrophoresis is limited and results in a restriction of the number of simultaneously analyzable samples. There is also room for improvement in the throughput In the case of detecting fluorescence from a capillary array with an image pickup device, such as a CCD or a CID (charge-injection device), the number of detectable capillary columns is limited due to limitation of the pixel number of the image pickup device. Furthermore, an image pickup device, such as a CCD or a CID, has a lower sensitivity than a photomultiplier.

In the case of employing a number of capillary columns, it is difficult to inject different samples into the respective columns. Furthermore, ends of the capillary columns must be dipped in samples contained in the sample injection vessels so that the samples are injected into the same by voltage application or the like, which are then transferred into reservoirs storing buffer solutions for electrophoresis. Thus, a great deal of time is required for injecting the samples and starting electrophoresis thereof, and it is therefore convenient if these operations can be automated.

While capillary electrophoresis apparatuses employing only a single capillary column are able to maintain at a constant temperature within that column, this is not the case with multi-capillary electrophoresis apparatuses. Therefore, electrophoresis speeds are dispersed due to temperature changes in electrophoresis, or the spaces between detected bases fluctuate (compression), and result in errors in base sequence determination.

A multi-capillary base sequence determining apparatus obtains four types of detection signals for respective fluorescence wavelengths, which are set to correspond with the end bases. The apparatus displays four types of signal waveforms for the respective end bases on the screen of a display unit, and displays what bases are currently being detected in the respective capillary columns during electrophoresis. If the detected waveforms are displayed as such in the case of making electrophoresis in a number of capillary columns, however, it is difficult to recognize which signal corresponds to each capillary column. Furthermore, it is also difficult to recognize which bases are currently detected in the respective capillary columns. Consequently, it is difficult to grasp the electrophoresis states.

SUMMARY OF THE INVENTION

The first object of the present invention is to improve throughput by increasing the number of capillary columns capable of making simultaneous electrophoresis and detection.

The second object of the present invention is to automatize operations from sample injection into a number of capillary columns prior to electrophoresis.

The third object of the present invention is to make it possible to readily grasp electrophoresis states of respective samples in real time.

In order to increase the number of capillary columns capable of making simultaneous electrophoresis and detection, the present invention comprises a multi-capillary array electrophoresis part, an excitation/photoreceiving optical system, and a scanning mechanism.

The multi-capillary array electrophoresis part includes a plurality of capillary columns charged with gels. One end of the capillary columns is two-dimensionally arranged to define a sample injection side, which the other ends are aligned with each other to define a detection part A plurality of samples containing different DNA fragments of four types of end bases are injected into the capillary columns one by one. Subsequently, an electrophoresis voltage is applied across the capillary columns for simultaneously electrophoresing the samples in all capillary columns. The DNA fragments of four types of end bases are identified with a plurality of types of fluorescent materials.

The excitation/photoreceiving optical system irradiates a surface of the capillary array with excitation light on a line perpendicular to the electrophoresis direction from a vertical direction on the detection part of the multi-capillary array electrophoresis part, for receiving and detecting fluorescence from the samples excited by the excitation light.

The scanning mechanism reciprocally moves the excitation/photoreceiving optical system along a straight line that is parallel to the surface of the capillary array on the detection part and perpendicular to the electrophoresis direction. The detection of the fluorescence from all capillary columns is carried out on the detection part of the multi-capillary array electrophoresis part.

According to a preferred aspect of the present invention, four types of DNA fragments of different end bases are labeled with different fluorescent materials respectively. The excitation/photoreceiving optical system preferably comprises an epi-optical system, a confocal optical system, a splitting spectro-optical system and photodetectors. The epi-optical system projects the excitation light to a single capillary column of the detection part by a condensation optical system and receives the fluorescence generated from the samples electrophoresed in the capillary column by the condensation optical system. The confocal optical system images the fluorescence generated from the samples electrophoresed in the capillary column along with the epi-optical system. The splitting spectro-optical system spatially splits fluorescence from a fluorescent image formed by the confocal optical system into four wavelengths corresponding to the four types of labeling fluorescent materials. The photodetectors detect these four fluorescent wavelengths.

When the DNA fragments are labeled with four types of fluorescent materials, reliability is improved. When the excitation/photoreceiving optical system comprises the epi-optical system and the confocal optical system, the structure is simplified and the scanning rate of the excitation/photoreceiving optical system can be increased. In this way, the scanning width is increased so that it is possible to increase the number of capillary columns, which are arranged on the detection part of the multi-capillary array electrophoresis part, i.e., the number of capillary columns for making simultaneous electrophoresis.

The photodetectors of the excitation/photoreceiving optical system are preferably prepared from photomultipliers or avalanche photodiodes. The speed of response or sensitivity of the photodetectors is affected by high-speed scanning, but both the speed of response and sensitivity are increased when compared with those of image pickup devices such as CCDs or CIDs when photomultipliers or avalanche photodiodes are employed as the photodetectors for coping with high-speed scanning. Consequently, simultaneous four-color fluorescence detection is enabled with a capillary array having about 500 capillary columns, depending on the outer diameters thereof, and remarkably increase the number of base sequences decoded at a time.

The first preferred aspect of the splitting spectro-optical system of the excitation/photoreceiving optical system comprises a lens system and four different fluorescence spectral filters for identifying the fluorescent materials. The lens system splits the fluorescence from the fluorescent image formed by the confocal optical system into four beams, and the four different fluorescence spectral filters are arranged on respective optical paths of the split beams.

The second preferred aspect of the splitting spectro-optical system of the excitation/photoreceiving optical system comprises a dispersion element and an optical system. The dispersion element separates the fluorescence from the fluorescent image formed by the confocal optical system into its spectral components. The optical system guides fluorescence of four wavelengths corresponding to the respective ones of labeling fluorescent materials, which have been separated into their spectral components by the dispersion element, to respective ones of the photodetectors.

In the case of the present invention, it is preferable to automatize operations for sample injection into a number of capillary columns prior to electrophoresis. Accordingly, two-dimensionally arranged capillary column ends are fixed in a downward position on the sample injection side of the multi-capillary array electrophoresis part A sample injection reservoir and an electrophoresis reservoir are arranged under the capillary column ends. The sample injection reservoir is provided with two-dimensionally arranged sample containers which correspond to the arrangement of the capillary column ends so that a voltage may be applied to the capillary columns. The electrophoresis reservoir stores an electrophoresis buffer solution so that a voltage is applied to all capillary columns. The multi-capillary electrophoresis apparatus in the present invention preferably comprises a reservoir moving mechanism for horizontally moving either reservoir for positioning the same under the capillary column ends, and vertically moving the reservoirs to and from the capillary column ends.

It is possible to automatize electrophoretic operations, including sample injection into the capillary column ends, by switching the sample injection reservoir and the electrophoresis reservoir by mean of the reservoir moving mechanism and bringing the same into contact with the capillary column ends.

In the case of the present invention, the multi-capillary electrophoresis apparatus preferably includes a means for preventing base sequence determination errors which result from temperature changes during electrophoresis. The multi-capillary electrophoresis apparatus would therefore further include a chamber for storing the multi-capillary array of the multi-capillary array electrophoresis part and a temperature control mechanism for maintaining the chamber at a constant temperature.

It is possible to maintain the multi-capillary electrophoresis apparatus in the present invention under controlled temperature conditions, eliminating compression resulting from fluctuation of the electrophoresis speed, thereby preventing errors in base sequence determination.

In an aspect for making it possible to readily grasp electrophoresis states of the respective samples in real time, two-dimensionally arranged capillary column ends are fixed in a downward position on the sample injection side of the multi-capillary array electrophoresis part, and a sample container and a electrophoresis reservoir are arranged under the capillary column ends so that either the sample container or the electrophoresis reservoir is selectively brought into contact with the capillary column ends. The sample container has two-dimensionally arranged wells which correspond to the arrangement of the capillary column ends so that a voltage may be applied to the respective capillary column ends inserted in the wells. The electrophoresis reservoir stores an electrophoresis buffer solution so that a voltage is applied to all capillary columns. The other end side of the capillary array is dipped in another buffer solution to which a voltage is applied, and an electrophoresis voltage is applied across the capillary array. The multi-capillary electrophoresis apparatus in the present invention comprises a data processor and a display unit. The data processor identifies bases detected in the respective capillary columns on the basis of detection results by the excitation/photoreceiving optical system. The display unit has a screen corresponding to the arrangement of the wells in the sample container, and displays identification results by the data processor by displaying the positions of the respective wells on the screen in four types of colors which correspond to the detected end bases.

Accurate real-time comprehension of the electrophoresis states is simplified by splitting electrophoresis signals into four colors corresponding to the end bases, and by displaying the same on the display screen in positions that correspond to the respective samples in the sample container.

The aforementioned in conjunction with the following detailed description and accompanying drawings will further clarify the present invention's features and advantages.

DESCRIPTION OF THE PREFERRED EMBODIMENTS

Figure 1:
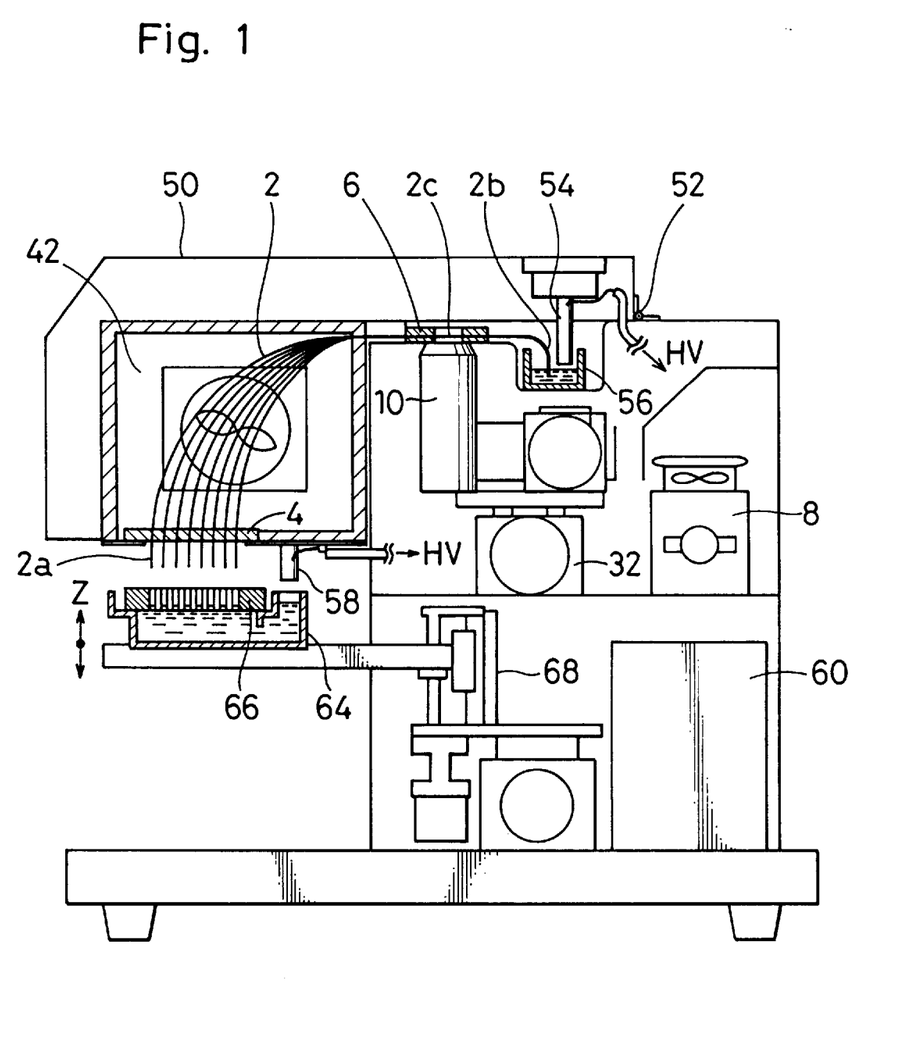
FIG. 1 is a side sectional view schematically showing an embodiment of the present invention.

FIG. 1 is a side sectional view schematically showing an embodiment of the present invention.

Capillary array 2 consists of a plurality of capillary columns, which are charged with gels of separation media. The lower end 2a of capillary array 2 defines the sample injection side. In the sample injection side, the capillary columns are two-dimensionally arranged and fixed by cassette holder 4 so as to be in contact with samples contained in a sample injection reservoir or a buffer solution stored in a lower reservoir for electrophoresis. The capillary columns are aligned on the upper end 2b of capillary array 2, to be in contact with an upper reservoir buffer solution also located in this area. Capillary array 2 is provided at upper end 2b with detection part 2c in which the capillary columns are aligned with each other and supported by cassette holder 6. Capillary array 2, cassette holder 4 (for two-dimensionally arranging lower ends of the capillary columns) and cassette holder 6 (for aligning the capillary columns with each other on detection part 2c) are shown in detail in FIG. 2.

Figure 2:
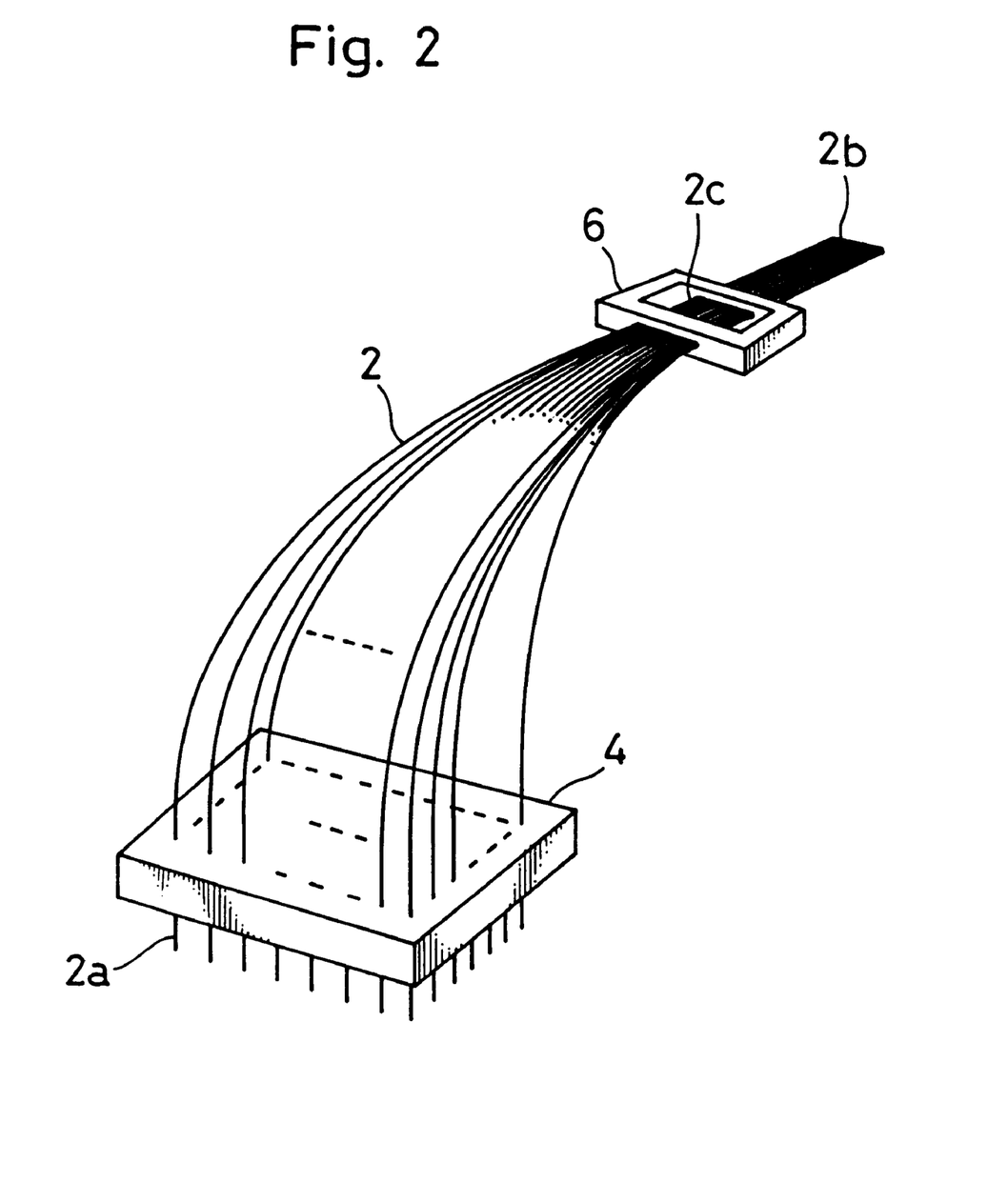
FIG. 2 is a perspective view showing a capillary array and a cassette holder.

Each capillary column is made of quartz glass or borosilicate glass, such as Pyrex, for example, and has an outer diameter of 200 to 300 $\mu$m and an inner diameter of 75 to 100 $\mu$m. The outer surface of this capillary column is preferably coated with a layer of a non-fluorescent material such as $SiO_2$ which does not generate fluorescence by excitation light in ultraviolet to near infrared regions or generates only a small amount of fluorescence which does not affect fluorescence measurement. Because of this, there is no need to remove the layer on detection part 2c. If each capillary column has a resin layer generating fluorescence, however, the layer is removed from detection part 2c. A plurality of, (e.g., 96 to 480) such capillary columns are arranged in capillary array 2.

Polyacrylamide gels, linear acrylamide gels or polyethylene oxide (PEO) gels are charged in the capillary columns as gels of separation media. Samples containing four types of DNA fragments labeled with four types of fluorescent materials selected from FAM, JOE, TAMRA, ROX, R6G, R-110 and the like with varied end bases are injected into the capillary columns to be simultaneously electrophoresed.

Argon gas laser unit 8 is provided as an excitation light source for exciting the labeling fluorescent materials. Argon gas laser unit 8 is a multi-line type laser unit having an output of 40 to 100 mW, and simultaneously oscillates laser beams having wavelengths of 488 nm, 514.5 nm and the like.

Figures 3A, 3B, 3C:
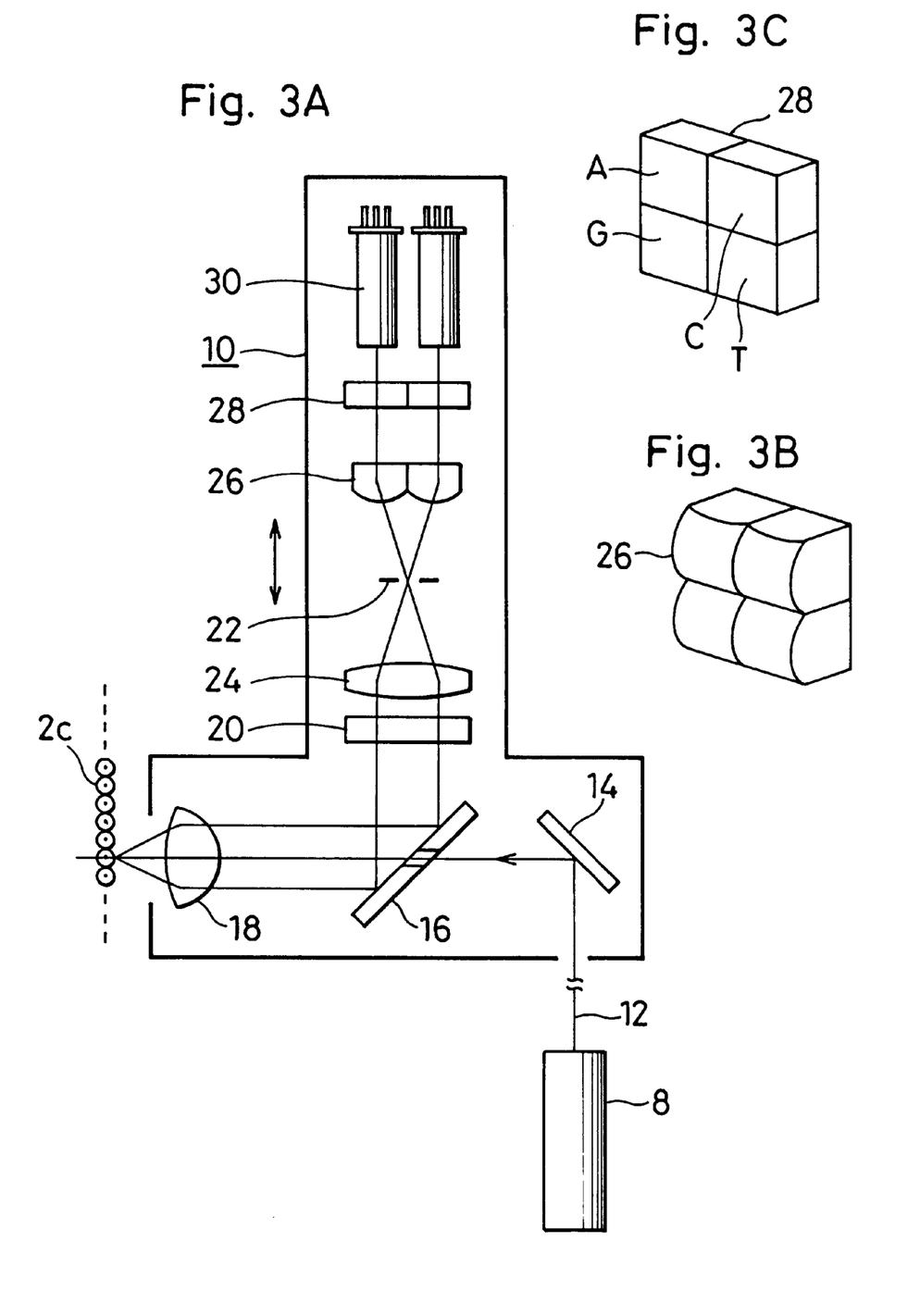
FIG. 3A is a side sectional view showing an excitation/photoreceiving optical system in the embodiment.
FIGS. 3B and 3C are perspective views showing a lens panel and a filter panel employed by the system.

FIG. 3A shows excitation/photoreceiving optical system 10 in detail. Numeral 14 denotes a mirror for perpendicularly irradiating a surface of detection part 2c of capillary array 2 with laser beam 12 from laser unit 8. Numeral 16 denotes a tunnel mirror having a hole in its center for transmitting an excitation light beam through the hole and reflecting fluorescence on a mirror face. Numeral 18 denotes a condenser lens for condensing and projecting excitation light on a single capillary column and receiving fluorescence generated from the samples electrophoresed in the capillary column. Condenser lens 18 is adapted to project the excitation light and receive the fluorescence, and forms an epi-optical system. The mirror face of tunnel mirror 16 reflects the fluorescence condensed by condenser lens 18.

Numeral 20 denotes an optical filter for blocking an excitation light component from the reflected light and transmitting the fluorescence. Numeral 22 denotes a pinhole slit for limiting a detection field, and numeral 24 denotes a diaphragm lens for imaging the fluorescence transmitted through optical filter 20 on the position of pinhole slit 22. A point generating the fluorescence in the capillary column is projected onto the position of pinhole slit 22, whereby a confocal optical system is formed. Optical filter 20, for removing the excitation light, can be prepared from an edge filter or colored glass. Pinhole slit 22 is adapted to prevent stray light penetration from adjacent capillary columns.

FIG. 3B shows lens panel 26, which is positioned to split the fluorescent image on pinhole slit 22 into four beams. Lens panel 26 can be manufactured by cutting and adhering single lenses to each other, or as a glass molding. FIG. 3C shows filter panel 28, consisting of different spectral filters for the respective labeling fluorescent materials, which are arranged on respective optical paths of the four split beams. Filter panel 28 is a bandpass filter in which four types of filters having different wavelength characteristics corresponding to the respective labeling fluorescent materials are arranged in parallel with each other on the respective optical paths. The transmission wavelengths of the respective filters correspond to emission wavelengths of the fluorescent materials labeling bases A, G, C and T respectively. Four photomultipliers 30 are arranged on the respective optical paths, in order to detect fluorescence transmitted through the respective filters.

Excitation/photoreceiving optical system 10 including mirror 14, tunnel mirror 16, condenser lens 18, optical filter 20, pinhole slit 22, diaphragm lens 24, lens panel 26, filter panel 28 and photomultipliers 30 is mounted on a stage of scanning mechanism 32. Excitation/photoreceiving optical system 10 is reciprocally moved along a straight line (perpendicular to the plane in FIG. 1 and vertical in FIG. 3A) which is parallel to the surface of capillary array 2 on detection part 2c and perpendicular to the electrophoresis direction in order to detect fluorescence from all capillary columns on detection part 2c. The direction for introducing laser beam 12 into mirror 14 is set to be parallel to the scan direction of excitation/photoreceiving optical system 10, so that an optical axis of laser beam 12 does not fluctuate even by the scanning of excitation/photoreceiving optical system 10.

Figure 4A:
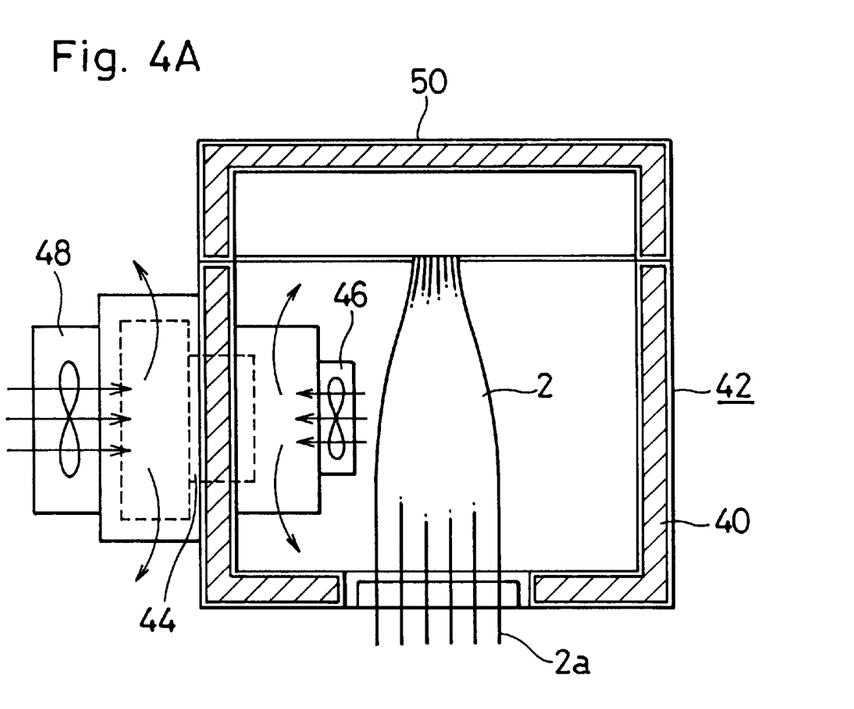
FIGS. 4A and 4B are front and side sectional views showing an electrophoresis chamber comprising a temperature control mechanism.
Figure 4B:
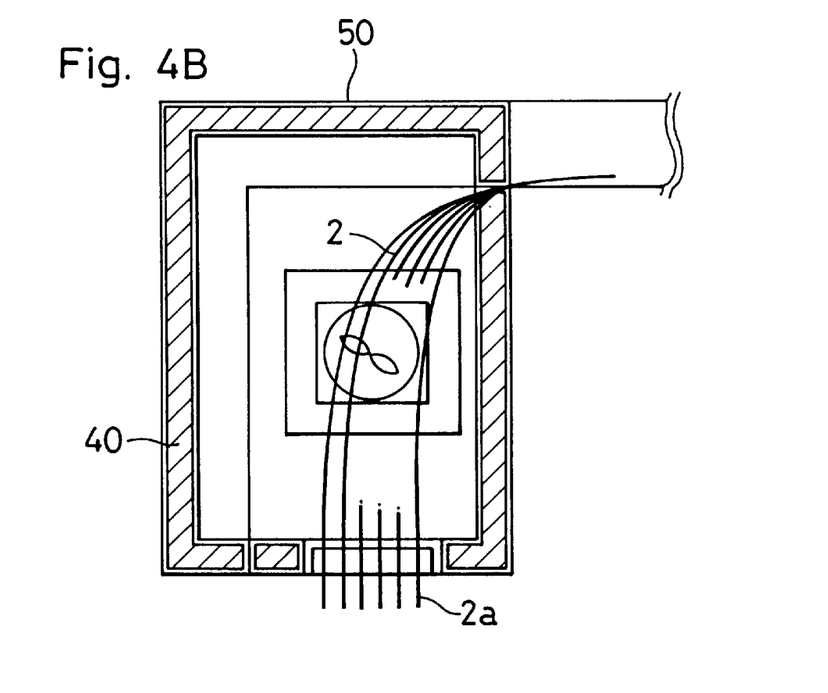

FIGS. 4A and 4B show electrophoresis chamber 42 enclosed with heat insulating material 40, such as polyurethane foam, for maintaining capillary array 2 at a constant temperature. Capillary array 2 is stored in this electrophoresis chamber 42. Electrophoresis chamber 42 is provided with Peltier element 44, for performing electronic heating/cooling. Numerals 46 and 48 denote inner and outer fans of Peltier element 44. Electrophoresis chamber 42 is provided with a platinum resistor or a thermocouple serving as a temperature sensor, so that the detection output of the temperature sensor is fed back to the Peltier element 44 and is PID-controlled, thereby maintaining a constant temperature in the interior of electrophoresis chamber 42.

Figure 5A:
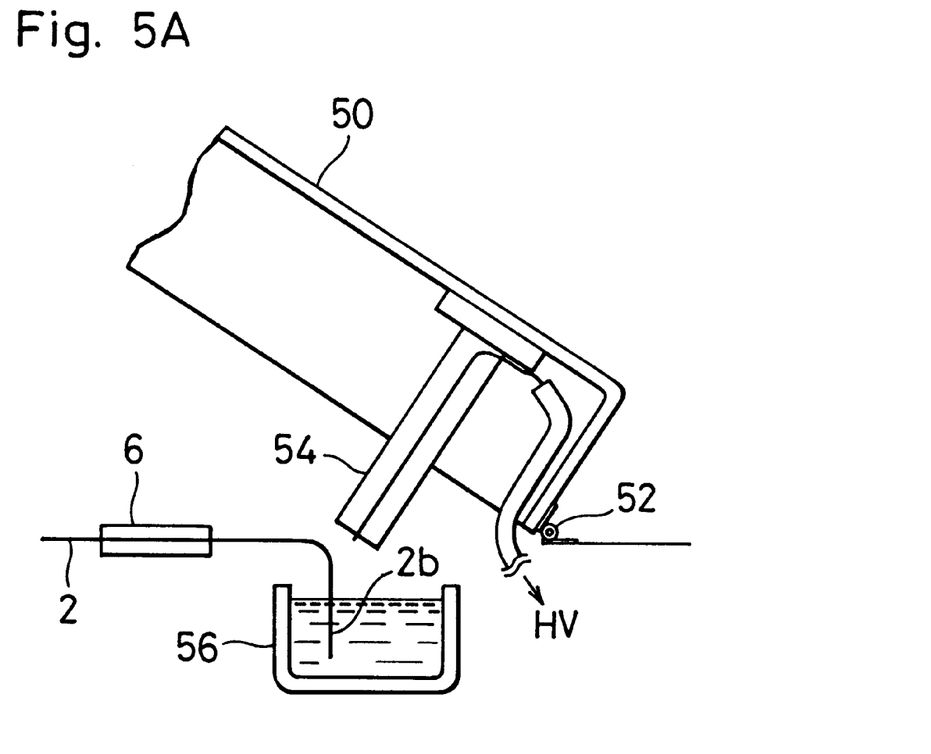
FIGS. 5A and 5B are side sectional views showing open and closed states of a cover of the electrophoresis chamber.
Figure 5B:
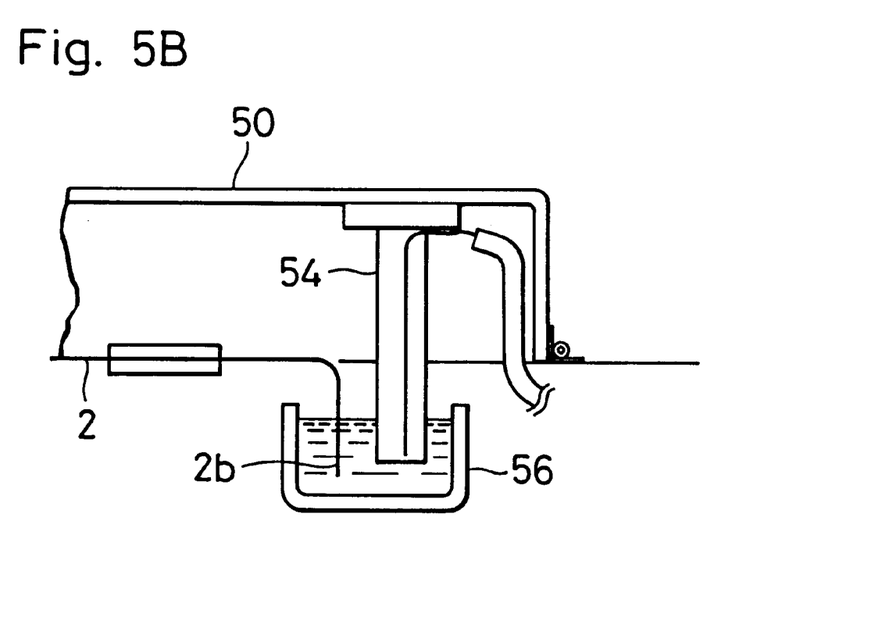

Cover 50 of electrophoresis chamber 42 can be opened/closed with a hinge 52 provided on its upper end, as shown in FIG. 5A. Upper electrode 54 is mounted on cover 50, so as to be in contact with a buffer solution stored in upper reservoir 56 along with cover 50, as shown in FIG. 5B. Upper end 2b of capillary array 2 is dipped in the buffer solution stored in upper reservoir 56. Lower electrode 58 is mounted on the lower side of electrophoresis chamber 42 as shown in FIG. 1. Lower electrode 58 is in contact with a buffer solution stored in sample injection reservoir 64 or electrophoresis lower reservoir 62, provided under the same, and conducts with lower end 2a of capillary array 2 when the buffer solution is pushed up to a position which provides contact with lower end 2a of capillary array 2. A sample injection voltage or a electrophoresis voltage is applied between the buffer solutions in reservoirs 62 and 64 from a high-voltage power supply unit of a power supply and control box 60 through electrodes 54 and 58. The power supply voltage is 30 kV, for example, and a current capacity is 10 to 30 mA.

Figure 6A:
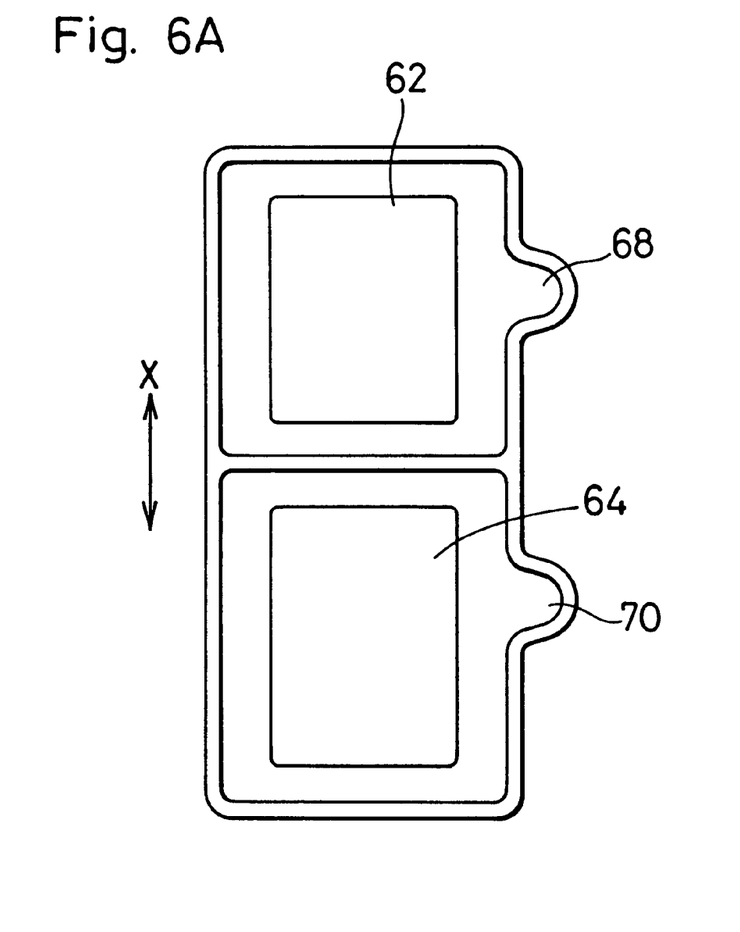
FIGS. 6A and 6B are a plan view and a side elevational view showing two reservoirs arranged on a lower side.
Figure 6B:
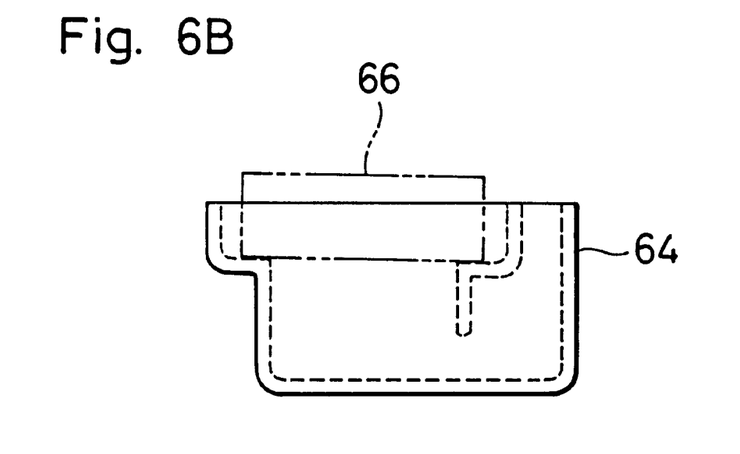

FIGS. 6A and 6B show two reservoirs 62 and 64 arranged on the lower side. Electrophoresis reservoir 62 and sample injection reservoir 64 are arranged in a horizontal plane and supported on X-Z sample stage 68. X-Z sample stage 68 provides movement in the horizontal direction (direction X: direction perpendicular to the plane of FIG. 1) for positioning either reservoir 62 or 64 under lower end 2a of capillary array 2, and movement in the vertical direction (direction Z: vertical in FIG. 1) for bringing the buffer solution stored in either reservoir 62 or 64 into contact with lower end 2a of capillary array 2, or separating the former from the latter.

Reservoirs 62 and 64 store the buffer solutions, and sample titer plate 66 formed with wells corresponding to the arrangement of capillary ends on lower end 2a of capillary array 2 is placed on reservoir 64. Membranes are extended on bottoms of the wells passing through sample titer plate 66, so that samples are adsorbed onto the membranes of the respective wells. The buffer solution stored in reservoir 64 comes into contact with the membranes SO that lower electrode 58 applies a voltage for sample injection to the capillary ends on lower end 2a of capillary array 2 through the buffer solution. Reservoirs 62 and 64 are provided with lower electrode spaces 68 and 70, so that lower electrode 58 entering spaces 68 and 70 comes into contact with the buffer solutions stored in reservoirs 62 and 64.

Sample titer plate 66, which provided with the membranes for adsorbing the samples on the bottoms of the wells passing through the same, may be replaced with that having bottomed wells and containing samples so that a electrophoresis voltage is applied to each well. In this case, reservoir 64 may store no buffer solution but lower electrode 58 can come into contact with electrodes of the wells when sample titer plate 66 is pushed up until the samples in the wells come into contact with lower end 2a of capillary array 2.

Figure 7:
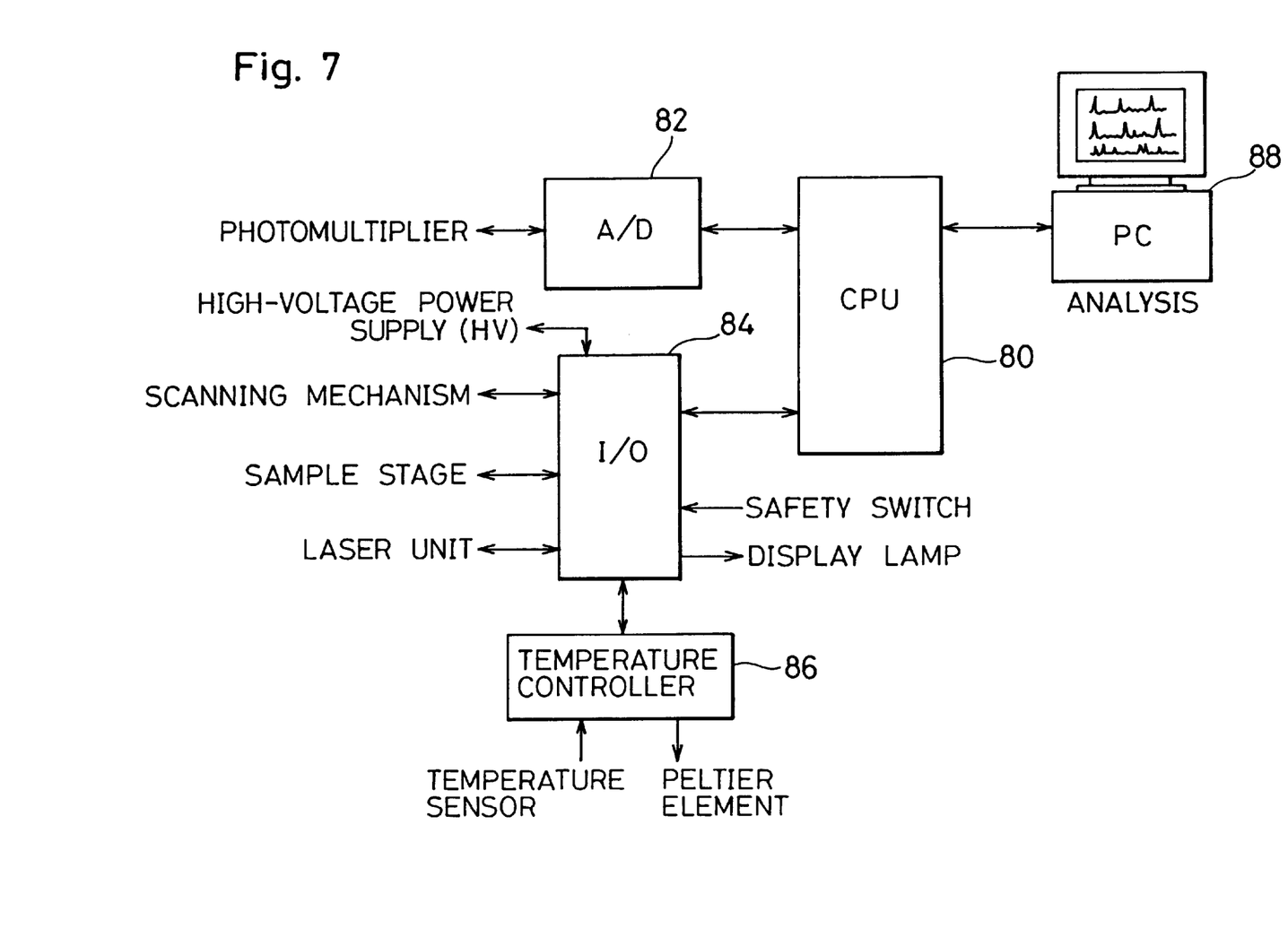
FIG. 7 is a block diagram showing a control board provided in a power supply and control box.

Power supply and control box 60 comprises a power supply unit for laser unit 8 and a control board in addition to the high-voltage power supply for sample injection and electrophoresis. The control board comprises CPU 80, A-D converter 82 for converting detection signals from photomultipliers 30 to digital signals and retrieves the same in CPU 80, I/O interface 84 for transferring and receiving signals to and from the respective parts by instructions from CPU 80, and temperature controller 86, which controls the temperature of electrophoresis chamber 42, as shown in FIG. 7. I/O interface 84 is connected with temperature controller 86, which controls the high-voltage power supply for sample injection and electrophoresis, a sensor and a motor of scanning mechanism 32, a sensor and a motor of X-Z sample stage 68, the power supply for laser unit 8, an interlocking safety switch, and a display lamp. CPU 80 is connected with external personal computer 88, which in turn performs data processing.

The operations of this embodiment are now described.

The samples are DNA fragment samples prepared through Sanger's reaction, and primers or terminators are labeled with different fluorescent materials in response to the types of the end bases. The samples are prepared in sample titer plate 66.

An acrylamide monomer solution or a monomer solution of gel material, composed primarily of acrylamide prepared in an electrophoresis gel composition, is negative pressure-sucked in the respective capillary columns of capillary array 2 through a vacuum pump or an aspirator, and gel-polymerized. Capillary array 2 is mounted on a prescribed position of the electrophoresis apparatus shown in FIG. 1 through cassette holders 4 and 6.

The buffer solutions are introduced into upper and lower reservoirs 56, 62 and 64, which in turn are mounted on the electrophoresis apparatus. Sample titer plate 66, which stores the samples, is mounted on lower reservoir 64 so that the samples are in contact with the buffer solution.

Thereafter personal computer 88 inputs a start instruction for sequencing so that sample stage 68 moves sample titer plate 66 to a position under capillary array end 2a and raises sample titer plate 66 in order to bring capillary array end 2a into contact with the samples stored in sample titer plate 66. Next, a high voltage is applied for a prescribed period of time across electrodes 54 and 58 for injecting the samples.

After the sample injection, sample stage 68 moves electrophoresis reservoir 62 to a position on capillary array end 2a for dipping capillary array end 2a in the electrophoresis buffer solution. A high voltage is then applied across electrodes 54 and 58, starting electrophoresis. During the electrophoresis, the interior of electrophoresis chamber 42 is kept at a constant temperature of 40 to 60° C., in order to prevent compression.

When the electrophoresed/separated DNA fragments pass through detection part 2c, excitation/photoreceiving optical system 10 is scanned to detect fluorescence from the fluorescent materials labeling the samples. At this time, the fluorescent labels are determined through the signal intensity ratios by the fluorescence passing through the four filters of filter panel 28 and detected by four photomultipliers 30 for identifying the bases. The scanning rate of excitation/photoreceiving optical system 10 is 250 to 500 mm/sec., and single scanning is preferably performed in a period of not more than 1 second.

Scanning mechanism 32 may be provided with an encoder so that identification of the capillary columns of capillary array 2 can be achieved through output pulses obtained from the encoder. The capillary column position obtained in this manner is compared with a fluorescence signal. Signals from the respective capillary columns are waveform-processed so that base sequences that correspond to the capillary columns may be determined through correction, such as mobility correction. The mobility correction is adapted to correct electrophoresis mobility levels, which may vary slightly from the molecular weights of the labeling fluorescent materials.

While reservoirs 56, 62 and 64, which store the buffer solutions, are mounted on the electrophoresis apparatus according to this embodiment, reservoirs 56, 62 and 64 may alternatively be located on the electrophoresis apparatus so that supply/discharge means for automatically injecting and discharging the buffer solutions into and from reservoirs 56, 62 and 64 through a nozzle or a port is provided on the electrophoresis apparatus, in order to automatize exchange of the buffer solutions.

Figure 8:
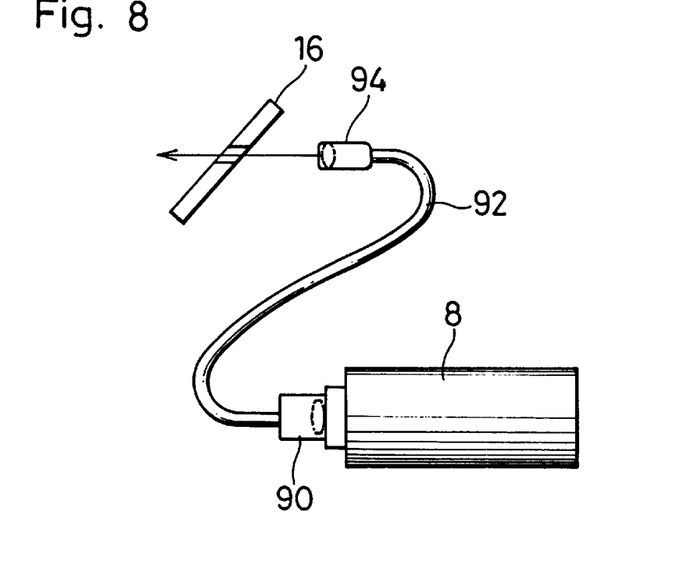
FIG. 8 is a plan view showing a mechanism for supplying an excitation light beam in another embodiment of the present invention.

FIG. 8 illustrates another embodiment of the present invention for providing an excitation light beam, which is emitted from laser unit 8 of an excitation light source, and which is not displaced by scanning of excitation/photoreceiving optical system 10. A laser beam from laser unit 8 is projected onto tunnel mirror 16, which is similar to that shown in FIG. 3, from collimator 94 through optical fiber member 92 coupled by coupler 90. Collimator 94 is fixed to scanned excitation/photoreceiving system 10.

In the embodiment shown in FIG. 8, the excitation light beam is not displaced by scanning of excitation/photoreceiving optical system 10 even if the direction of laser unit 8 is not strictly set.

Figure 9:
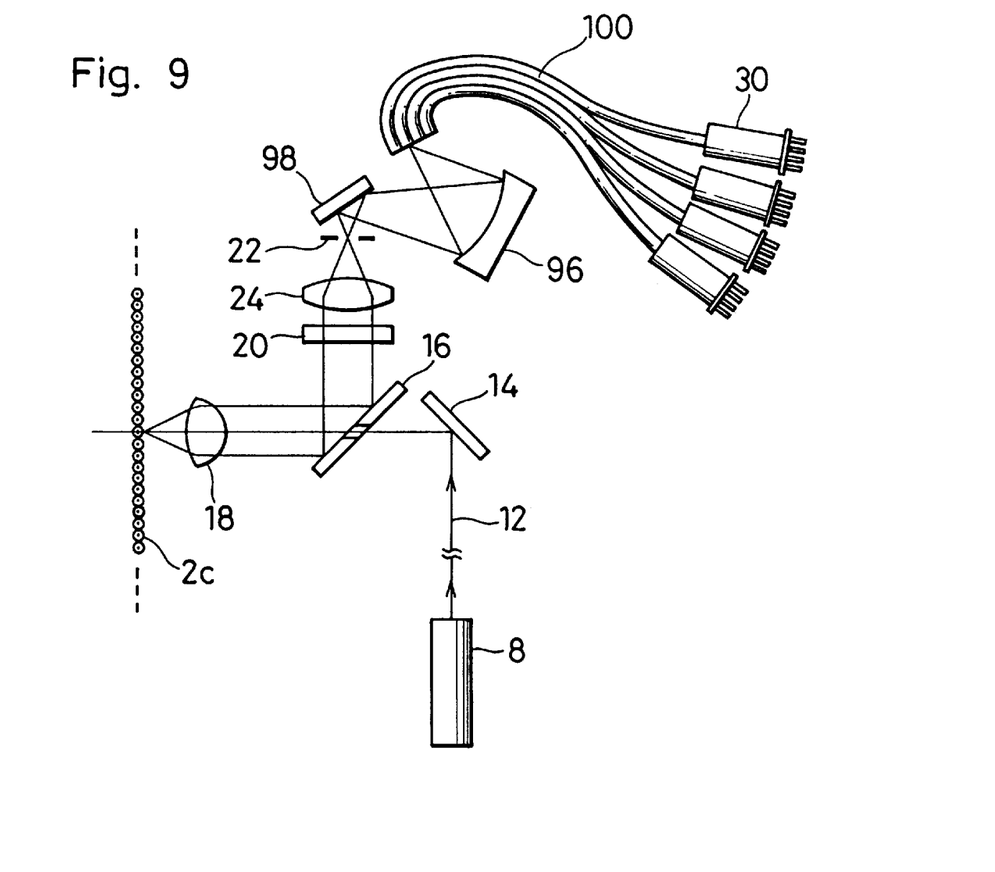
FIG. 9 is a side sectional view showing an excitation/photoreceiving optical system in still another embodiment of the present invention.

FIG. 9 shows still another embodiment of a splitting spectro-optical system in excitation/photoreceiving optical system 10. While lens panel 26 and filter panel 28 are employed in the embodiment shown in FIG. 3 for separating the fluorescence imaged on pinhole slit 22 into its spectral components after splitting the same into four, concave grating 96 simultaneously splits and separates a fluorescent image formed on pinhole slit 22. Numeral 98 denotes a plane mirror for reflecting fluorescence transmitted through pinhole slit 22 toward concave grating 96. An end of bundle fiber member 1 O0 for receiving fluorescence from wavelength positions corresponding to four labeling fluorescent materials is arranged on a spectral imaging position by concave grating 96, and the other end of bundle fiber member 10 is guided to four photomultipliers or avalanche photodiodes 30.

Figure 10:
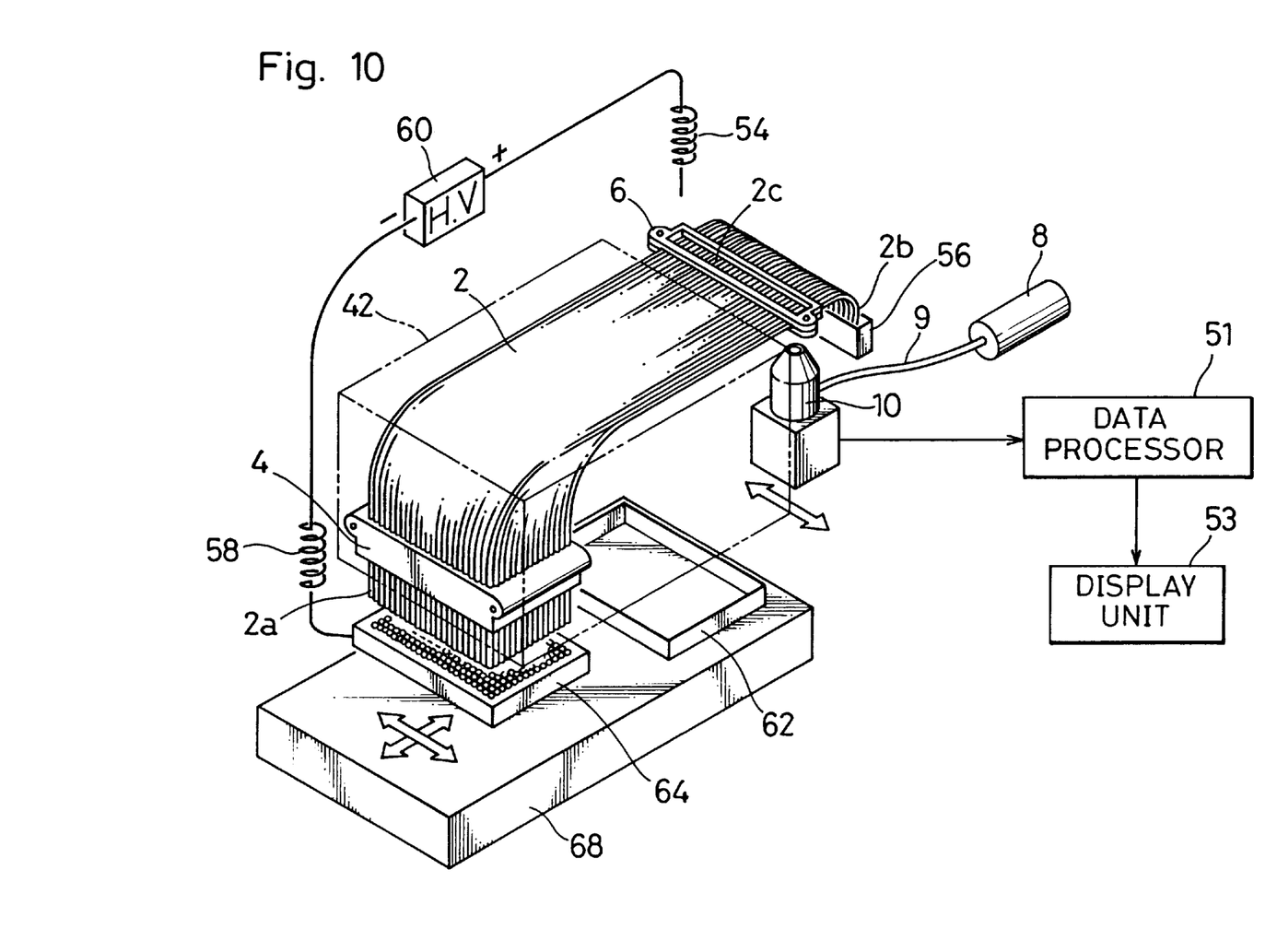
FIG. 10 is a perspective view schematically showing another embodiment of the present invention.

FIG. 10 is a perspective view schematically showing anther embodiment for making it possible to readily grasp electrophoresis states of respective samples in real time.

The multi-capillary array electrophoresis part, excitation/photoreceiving optical system 10 and scanning mechanism of this embodiment are nearly identical to those shown in FIGS. 1, 3A, 3B and 3C. Capillary columns on sample injection side 2a of capillary array 2 are two-dimensionally arranged and fixed by cassette holder 4, and positioned to be in contact with samples contained in wells of sample plate 64 or a buffer solution stored in lower reservoir 62 for electrophoresis. Samples containing four types of DNA fragments labeled with four types of fluorescent materials selected from different fluorescent materials FAM, JOE, TAM RA, ROX, ABI, R6G and R-110 varied with end bases or four types of DNA fragments coded by employing two types of fluorescent materials at different ratios similarly to reference 2 are injected into the capillary columns to be simultaneously electrophoresed.

Argon gas laser unit 8 is provided as an excitation light source for exciting the labeling fluorescent materials. Argon gas laser unit 8 is a multi-line type laser unit having an output of 40 to 100 mW, and simultaneously oscillates laser beams of two types of wavelengths of 488 nm and 514.5 nm. Excitation/photoreceiving optical system 10 is adapted to irradiate the capillary columns with argon laser beams which serves as excitation light on detection part 2c for detecting fluorescence from the samples. It is scanned in a direction, which is parallel to the surface of capillary array, 2 and perpendicular to a electrophoresis direction, as shown in FIG. 3. The laser beams from laser unit 8 are guided to excitation/photoreceiving optical system 10 through optical fiber member 9 which is attached by means of a coupler, so that the excitation light beams from laser unit 8 are not displaced by scanning of excitation/photoreceiving optical system 10.

Capillary array 2 is stored in electrophoresis chamber 42, and is maintained at a constant temperature.

Electrophoresis reservoir 62 and sample plate 64, serving as a sample container, are supported in line on X-Y-Z movable stage 68 in a horizontal plane under lower end 2a of capillary array 2. Movable stage 68, provides movement in the horizontal direction (direction X or Y) for locating either reservoir 62 or sample plate 64 under lower end 2a of capillary array 2, and movement in the vertical direction (direction Z) for bringing together or separating the samples contained in the wells of sample plate 64 or the buffer solution stored in reservoir 62.

Sample plate 64 comprises 384 wells, i.e. 24 by 16 wells which are regularly arranged in the vertical and transverse directions, and the arrangement of capillary ends on lower end 2a of capillary array 2 corresponds to the well arrangement of sample plate 64. Sample plate 64 can be prepared so that bottoms of the wells pass through the same and membranes are extended beyond the bottoms for adsorbing the samples. Sample plate 64 is placed on reservoir 62 storing the buffer solution so that the membranes are in contact with the buffer solution, whereby a voltage for sample injection can be applied to the capillary ends on lower end 2a of capillary array 2 through the buffer solution.

Reservoir 62 stores the buffer solution for electrophoresis, so that a electrophoresis voltage can be applied to the capillary ends on lower end 2a of capillary array 2 through the buffer solution.

Sample plate 64, provided with the membranes for adsorbing the samples on the bottoms of the wells passing through the same, may be replaced with another having bottomed wells which contain samples so that the electrophoresis voltage is applied to each well.

Upper electrode 54 is in contact with a buffer solution stored in upper reservoir 56 and lower electrode 58 is positioned so as to be in contact with the buffer solution stored in lower reservoir 62 or, alternatively, the samples contained in the wells of sample plate 64, while high-voltage power supply 60 applies a voltage in sample injection or in electrophoresis to electrodes 54 and 58. The voltage is 30 kV, for example, and a current is 10 to 30 mA.

A data processor 51 is provided for distinguishing bases detected in the respective capillary columns based on detection results by the excitation/photoreceiving optical system 10 which distinguishes bases from each other and determines base sequences. A display unit 53, such as a CRT (cathode ray tube) is used for displaying the results of data processor 51.

The illustration in FIG. 8 is used as an optical system for guiding excitation light to excitation/photoreceiving optical system 10. The laser beams from laser unit 8, which serves as an excitation light source, are projected onto tunnel mirror 16 from collimator 94 through optical fiber member 92 attached by coupler 90. Collimator 94 is fixed to the scanned excitation/photoreceiving optical system 10, and laser unit 8 is fixed onto the exterior of excitation/photoreceiving optical system 10. Collimator 94 is positions so as to irradiate the surface of detection part 2c of capillary array 2 with the laser beams. The remaining optical systems of excitation/photoreceiving optical system 10 are identical to those shown in FIGS. 3A to 3C. As an exemplary operation, DNA fragment samples labeled with four types of fluorescent materials are electrophoresed.

Although not shown in FIG. 10, this electrophoresis apparatus comprises a high voltage power supply for sample injection and electrophoresis, a power supply for laser unit 8 and a control board. The control board, which is identical to that shown in FIG. 7, comprises CPU 80, A-D converter 82 for converting detection signals from photomultipliers 30 to digital signals and retrieving the same in CPU 80, I/O interface 84 for transferring and receiving signals to and from the respective parts by instructions from CPU 80, and temperature controller 86 for controlling the temperature of electrophoresis chamber 42. I/O interface 84 is connected with temperature controller 86, the high-voltage power supply for sample injection and electrophoresis, a sensor and a motor of scanning mechanism 32, a sensor and a motor of X-Y-Z movable stage 68, the power supply for laser unit 8, an interlocking safety switch, and a display lamp. CPU 80 is connected with external personal computer 88. Personal computer 88 corresponds to data processor 51 shown in FIG. 10, and its display corresponds to display unit 53.

Operations of this embodiment are now described.

The samples are DNA fragment samples prepared through Sanger's reaction, and primers or terminators are labeled with different fluorescent materials according to the types of end bases. The samples are prepared in sample plate 66.

The capillary columns of capillary array 2 are charged with gels, and mounted on prescribed positions of the electrophoresis apparatus shown in FIG. 10 by cassette holders 4 and 6.

The buffer solutions are introduced into upper and lower reservoirs 56 and 62, which in turn are mounted on the electrophoresis apparatus. Assuming that sample plate 64 containing the samples has wells passing therethrough so that membranes are extended beyond bottoms thereof for adsorbing the samples, sample plate 64 is mounted on still another reservoir so that the samples are in contact with a buffer solution stored in this reservoir.

Thereafter, personal computer 88 inputs a start instruction for sequencing so that movable stage 68 moves sample plate 64 to a position under capillary array end 2a and raises sample plate 64 in order to bring capillary array end 2a into contact with the samples stored in sample plate 64. A high voltage is then applied across electrodes 54 and 58 for injecting the samples.

After the sample injection, movable stage 68 moves electrophoresis reservoir 62 to a position under capillary array end 2a for dipping capillary array end 2a in the buffer solution stored in electrophoresis reservoir 62. A high voltage is then applied across electrodes 54 and 58 for starting electrophoresis. During the electrophoresis, the interior of electrophoresis chamber 42 is kept at a constant temperature of 40 to 60° C. In order to prevent compression.

Figure 11A:
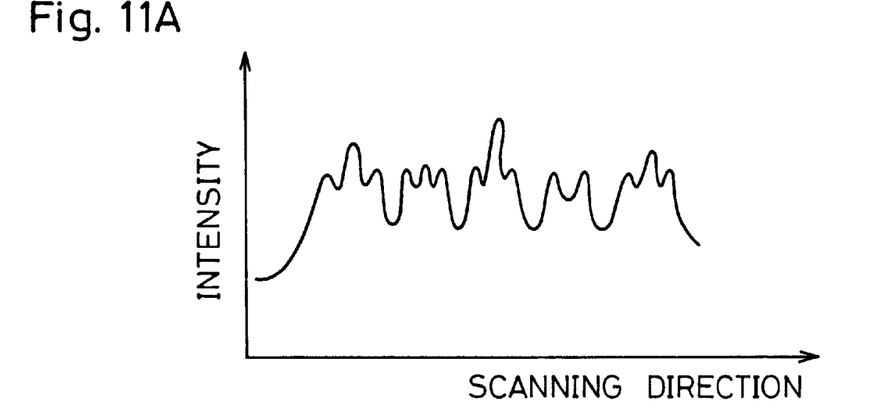
FIG. 11A is a waveform diagram showing a fluorescence signal obtained from a single photomultiplier.
Figure 11B:
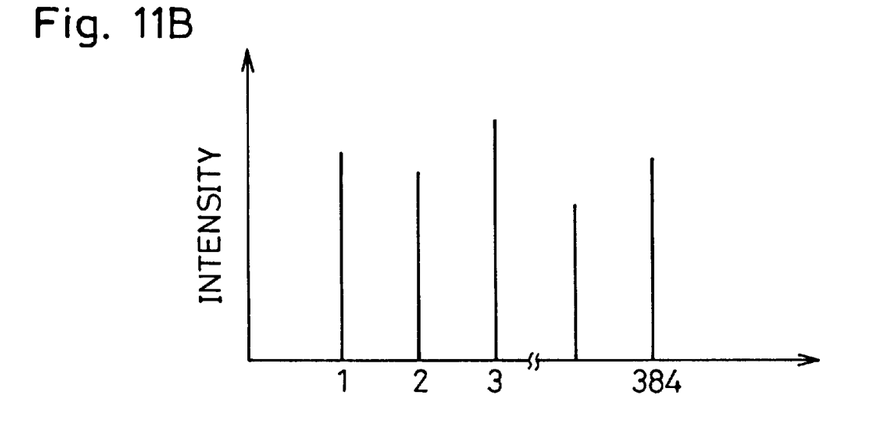
FIG. 11B is a waveform diagram of signals of only DNA fragment samples extracted from the fluorescence signal.

When the electrophoresed/separated DNA fragments pass through detection part 2c, excitation/photoreceiving optical system 10 is scanned to detect fluorescence from the fluorescent materials labeling the samples. At this time, signals by fluorescence passing through four filters of filter panel 28 and detected by four photomultipliers 30 are obtained as shown in FIG. 11A. The signals shown in FIG. 11A are obtained in four sets according to the types of end bases of the DNA fragment samples. These signals are retrieved in personal computer 88, which is a data processor through the A-D converter. These signals are compared with signals when the DNA fragment samples are not migrating, and signals of only the DNA fragment samples are extracted as shown in FIG. 11B. Following this, bases having the maximum intensity in the four sets of signals, and which correspond to signals exceeding a constant threshold value, are recognized as the bases in the respective capillary columns.

Figure 11C:
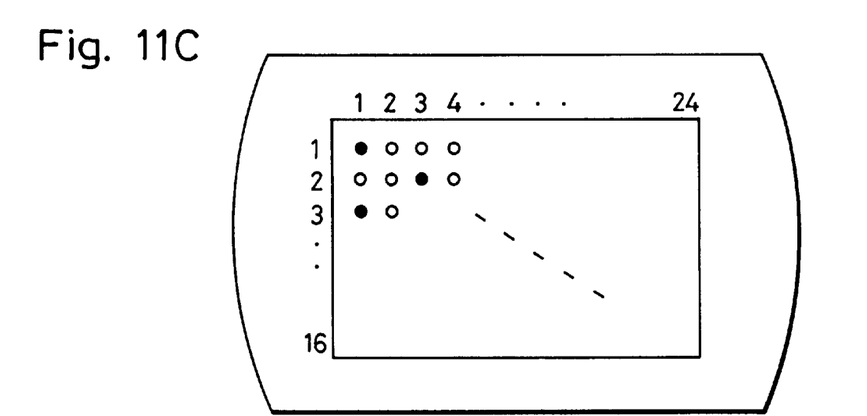
FIG. 11C is a schematic front elevational view showing an exemplary display screen.

Identification of the capillary columns in capillary array 2 can be performed by providing an encoder in a scanning mechanism for scanning excitation/photoreceiving optical system 10, and examining output pulses obtained from the encoder. Capillary column positions obtained in this manner are combined with the types of the bases obtained from fluorescence signals, to be displayed in four types of colors which relate to the end bases on a display screen corresponding to the well arrangement of sample plate 64, as shown in FIG. 11C.

Excitation/photoreceiving optical system 10 is not restricted to that shown in FIGS. 3A to 3C. For example, system 10 may simultaneously split and separate a fluorescent image formed on pinhole slit 22 by a concave grating, while a bundled fiber end receiving fluorescence from wavelength positions, corresponding to four labeling fluorescent materials, may be arranged on a spectral imaging position so that the other end of the bundled fiber member is guided to four photomultipliers.

Although the present invention has been described and illustrated in detail, it must be clearly understood that this is only an illustration and example only and is not to be seen as limited, the spirit and scope of the present invention is limited only by the terms of the appended claims.

What is claimed is:

1. A multi-capillary electrophoresis apparatus comprising:
   a multi-capillary array electrophoresis part including a plurality of capillary columns charged with gels having their beginning ends two-dimensionally arranged to define a sample injection side and the other side of their ends aligned with each other to define a detection part, for injecting a plurality of samples containing four types of DNA fragments of different end bases which are distinguished from one another by labeling them with a plurality of types of fluorescent materials into said capillary columns one by one, and being exposed to an electrophoresis voltage for simultaneously electrophoresing said samples in all said capillary columns,
   said four types of DNA fragments of said different end bases are labeled with different said fluorescent materials;
   an excitation/photoreceiving optical system for irradiating a surface of said capillary array by excitation light on a line that is perpendicular to an electrophoresis direction from a vertical direction on the detection part of said multi-capillary array electrophoresis part, and for receiving and detecting fluorescence from said samples being excited by said excitation light;
   said excitation/photoreceiving optical system comprising:
   (a) an epi-optical system for projecting said excitation light to a single said capillary column on said detection part by a condensation optical system while receiving said fluorescence generated from said samples being electophoresed in said capillary columns by said condensation optical system;
   (b) a confocal optical system for imaging said fluorescence generated from said samples being electophoresed in said capillary columns along with said epi-optical system;
   (c) a splitting spectro-optical system for spatially splitting fluorescence from an fluorescent image which is formed by said confocal optical system into four respective wavelengths corresponding to four types of said labeling fluorescent materials;
   said splitting spectro-optical system of said excitation/photoreceiving optical system comprises a lens panel for splitting said fluorescence from said fluorescent image being formed by said confocal optical system into four beams and four different fluorescence spectral filters for labeling fluorescent materials which are arranged on respective optical paths of said split beams; and
   (d) photodetectors for detecting said fluorescence which is split into four;
   a scanning mechanism for reciprocally moving said excitation/photoreceiving optical system along a straight line which is parallel to the surface of said capillary array on said detection part, and perpendicular to the electrophoresis direction for detecting fluorescence from all the capillary columns on the detection part of said multi-capillary array electrophoresis part, wherein
   two-dimensionally arranged capillary column ends are fixed in a position on said sample injection side of said multi-capillary array electrophoresis part, a sample injection reservoir provided with two-dimensionally arranged sample containers which correspond to the arrangement of said capillary column ends so that a voltage may be applied to said capillary columns through respective samples in said sample containers, and a electrophoresis reservoir storing a electrophoresis buffer solution so that a voltage may be applied to all said capillary columns are arranged under said capillary column ends,
   said multi-capillary electrophoresis apparatus also comprising a reservoir moving mechanism for horizontally moving either said reservoir for positioning the same under said capillary column ends and vertically moving said reservoirs to and from said capillary column ends.

2. The multi-capillary electrophoresis apparatus in accordance with claim 1, wherein
   said photodetectors of said excitation/photoreceiving optical system are photomultipliers or avalanche photodiodes.

3. The multi-capillary electrophoresis apparatus in accordance with claim 1, wherein
   said lens system is a lens panel obtained by adhering four single lenses to each other.

4. The multi-capillary electrophoresis apparatus in accordance with claim 1, wherein
   said lens system is a lens panel molding having four lenses.

5. The multi-capillary electrophoresis apparatus in accordance with claim 1, wherein
   said splitting spectro-optical system of said excitation/photoreceiving optical system comprises a dispersion element for separating said fluorescence from said fluorescent image formed by said confocal optical system into its spectral components, and an optical system for guiding said fluorescence of four wavelengths, which have been separated into its spectral components by said dispersion element corresponding to said labeling fluorescent materials, to respective ones of said photodetectors.

6. The multi-capillary electrophoresis apparatus in accordance with claim 1, wherein said excitation light which is applied from said excitation/photoreceiving optical system to said capillary array is supplied from a light source optical system on the exterior of said excitation/photoreceiving optical system as a beam which travels in a direction parallel to the scanning direction of said excitation/photoreceiving optical system so that an optical axis of an excitation light beam supplied from said light source optical system is not affected by scanning of said excitation/photoreceiving optical system.

7. The multi-capillary electrophoresis apparatus in accordance with claim 1, wherein said excitation light being applied from said excitation/photoreceiving optical system to said capillary array is supplied from a light source optical system on the exterior of said excitation/photoreceiving system through an optical fiber member so that an optical axis of an excitation light beam supplied from said light source optical system is not affected by scanning of said excitation/photoreceiving optical system.

8. The multi-capillary electrophoresis apparatus in accordance with claim 1, further comprising:

a chamber for storing a multi-capillary array of said multi-capillary array electrophoresis part, and a temperature control mechanism for maintaining said chamber at a constant temperature.

9. The multi-capillary electrophoresis apparatus in accordance with claim 1, wherein the outside surface of said capillary columns are coated with layers of a non-fluorescent material which does not generate fluorescence by excitation light in ultraviolet to near infrared regions or generates only a small amount of fluorescence, which does not affect fluorescence measurement.

10. The multi-capillary electrophoresis apparatus in accordance with claim 1, wherein the outside surface of said capillary columns are coated with layers of a fluorescent material, which generates fluorescence by excitation light in ultraviolet to near infrared regions, and said layers are removed from said detection part.

11. A multi-capillary electrophoresis apparatus comprising:

a multi-capillary array electrophoresis part including a plurality of capillary columns charged with gels having their beginning ends two-dimensionally arranged to define a sample injection side and the other side of their ends aligned with each other to define a detection part, for injecting a plurality of samples containing four types of DNA fragments of different end bases which are distinguished from one another by labeling them with a plurality of types of fluorescent materials into said capillary columns one by one, and being exposed to an electrophoresis voltage for simultaneously electrophoresing said samples in all said capillary columns;

an excitation/photoreceiving optical system for irradiating a surface of said capillary array by excitation light on a line that is perpendicular to an electrophoresis direction from a vertical direction on the detection part of said multi-capillary array electrophoresis part, and for receiving and detecting fluorescence from said samples being excited by said excitation light;

said excitation/photoreceiving optical system comprising:

(a) an epi-optical system for projecting said excitation light to a single said capillary column on said detection part by a condensation optical system while receiving said fluorescence generated from said samples being electrophoresed in said capillary columns by said condensation optical system;

(b) a confocal optical system for imaging said fluorescence generated from said samples being electrophoresed in said capillary columns along with said epi-optical system;

(c) a splitting spectro-optical system for spatially splitting fluorescence from an fluorescent image which is formed by said confocal optical system into four respective wavelengths corresponding to four types of said labeling fluorescent materials;

said splitting spectro-optical system of said excitation/photoreceiving optical system comprises a lens panel for splitting said fluorescence from said fluorescent image being formed by said confocal optical system into four beams and four different fluorescence spectral filters for labeling fluorescent materials which are arranged on respective optical paths of said split beams; and (d) photodetectors for detecting said fluorescence which is split into four; and a scanning mechanism for reciprocally moving said excitation/photoreceiving optical system along a straight line which is parallel to the surface of said capillary array on said detection part, and perpendicular to the electrophoresis direction for detecting fluorescence from all the capillary columns on the detection part of said multi-capillary array electrophoresis part, wherein two-dimensionally arranged capillary column ends are fixed in a position on said sample injection side of said multi-capillary array electrophoresis part, and a sample container having two-dimensionally arranged wells which correspond to the arrangement of said capillary column ends so that a voltage may be applied to respective said capillary column ends which are inserted in samples in said wells and a electrophoresis reservoir storing a electrophoresis buffer solution so that a voltage may be applied to all said capillary columns are arranged under said capillary column ends so that either said sample container or said electrophoresis reservoir is selectively brought into contact with said capillary column ends, while the other end of said capillary array electrophoresis part is dipped in another buffer solution to which a voltage is applied, and an electrophoresis voltage is applied across said capillary array electrophoresis part, said multi-capillary electrophoresis apparatus also comprising;

a data processor for identifying bases being detected in respective said capillary columns on the basis of detection results by said excitation/photoreceiving optical system for deciding base sequences, and a display unit having a screen which corresponds to the arrangement of said wells in said sample container for displaying positions of respective said wells on said screen in four types of colors in response to detected said end bases.

* * * * *